(12) United States Patent
Singh et al.

(10) Patent No.: US 6,544,562 B2
(45) Date of Patent: Apr. 8, 2003

(54) ACNE TREATMENT INCLUDING DUAL-PACKAGE SYSTEM

(75) Inventors: Mohinder Singh, Naperville, IL (US); Michael A. Wojcik, Plainfield, IL (US)

(73) Assignee: Blistex Inc., Oak Brook, IL (US)

( * ) Notice: Subject to any disclaimer, the term of this patent is extended or adjusted under 35 U.S.C. 154(b) by 0 days.

(21) Appl. No.: 09/888,767

(22) Filed: Jun. 25, 2001

(65) Prior Publication Data

US 2003/0008851 A1 Jan. 9, 2003

(51) Int. Cl.[7] .................. A61K 35/78; A61K 9/00; A01N 39/00; A01N 37/36
(52) U.S. Cl. .............. 424/725; 424/400; 424/616; 435/810; 514/159; 514/859
(58) Field of Search ................. 424/725, 616, 424/400; 514/159, 859; 435/810

(56) References Cited

U.S. PATENT DOCUMENTS 4,355,028 A * 10/1982 Kligman et al.
5,470,884 A * 11/1995 Corless et al.
6,200,964 B1 * 3/2001 Singleton et al.

FOREIGN PATENT DOCUMENTS

WO   WO 99/02133   *   1/1999

OTHER PUBLICATIONS

Bollinger et al., J Pharm Sci (1977); 66(5): 718–722. Benzoyl peroxide stability in pharmaceutical gel preparations.*

* cited by examiner

Primary Examiner—Christopher R. Tate
Assistant Examiner—Michele C. Flood
(74) Attorney, Agent, or Firm—Arnstein & Lehr

(57) ABSTRACT

A dual regimen acne treatment package includes an outer container, and disposed within the outer container first and second inner containers which are separate from each other. Each of the inner containers has an exposed dispensing means, the first inner container containing a solubilized salicylic acid acne treatment composition, and the second inner container containing a solubilized benzoyl peroxide acne treatment composition.

8 Claims, 3 Drawing Sheets

ACNE TREATMENT INCLUDING DUAL-PACKAGE SYSTEM

BACKGROUND OF THE INVENTION

1. Field of the Invention

The invention relates to the field of over-the-counter acne treatment compositions.

2. Description of Related Art

Compositions for treatment of acne vulgaris, white heads, black heads and comedones are well known. Generally, such compositions include a keratolytic agent, such as salicylic acid, which dissolves the intracellular matrix of the treated lesion and causes the lesion to slough off the body as dead tissue.

Salicylic acid has been approved by the US Food and Drug Administration for treatment of acne in concentrations of 0.5 to 2% by weight. Such compositions may be in the form of a gel, lotion, cream or solution to be applied with pads.

Salicylic acid is sparingly soluble in water, 1 gram dissolving in about 460 ml of water at room temperature (about 0.2% by weight), to produce a solution with a pH of 2.4. Salicylic acid has a far greater solubility in alcohol, 1 gram dissolving in about 2.7 ml, so most acne treatment compositions are based on a mixture of alcohol and water. The presence of alcohol permits a far greater solubility of salicylic acid than would be possible with water alone.

Benzoyl peroxide is approved by the US Food and Drug Administration for treatment of acne in concentrations of 2.5 to 10% by weight. Benzoyl peroxide is, however, sparingly soluble in both water and alcohol, and is usually provided in the form of creme-type products where it is in suspension form. Benzoyl peroxide increases the epithelial cell growth rate, leading to an increased sloughing rate. This increase results in a larger structure of the follicular plugs, and promotes resolution of comedones. Benzoyl peroxide also has an oxidizing potential which may contribute to bacteriostatic and bacteriocidal activity, suppressing the local population of propiolibacterium acnes.

Benzoyl peroxide is one of the most effective topical nonprescription medications available for acne.

Because the actions of salicylic acid and benzoyl peroxide are slightly different, alternate applications are useful in treatment of acne. However, alternate applications have heretofore required purchase of two different products and following instructions which may not be associated with either product.

SUMMARY OF THE INVENTION

Is therefore an object of the invention to make it possible to provide a dual composition an acne treatment regimen in a single package.

It is another object of the invention to provide in a single package different morning and evening treatments for acne.

It is a further object of the invention to provide in a single package a clear gel morning treatment which can unclog pores and keep pores open due to keratolytic action, and a lotion evening treatment which penetrates, kills bacteria, reduces skin surface fatty acids, helps prevent pimples and prevents them from further spreading.

In order to achieve these and other objects, the invention is directed to a dual regimen acne treatment package comprising an outer container, disposed within the outer container first and second inner containers which are separate from each other, each of said inner containers having an exposed dispensing means, the first said inner container containing a solubilized salicylic acid acne treatment composition, and the second said inner container containing a solubilized benzoyl peroxide acne treatment composition.

Preferably, the dispensing means for the treatment compositions is a pump. However, other dispensing means may also be used, including aerosol and applicator pads. Both dispensing means need not be of the same type.

Preferably, the outer container is fitted with at least one cap covering and protecting the dispensing means.

DESCRIPTION OF THE PREFERRED EMBODIMENTS

Figure 1:
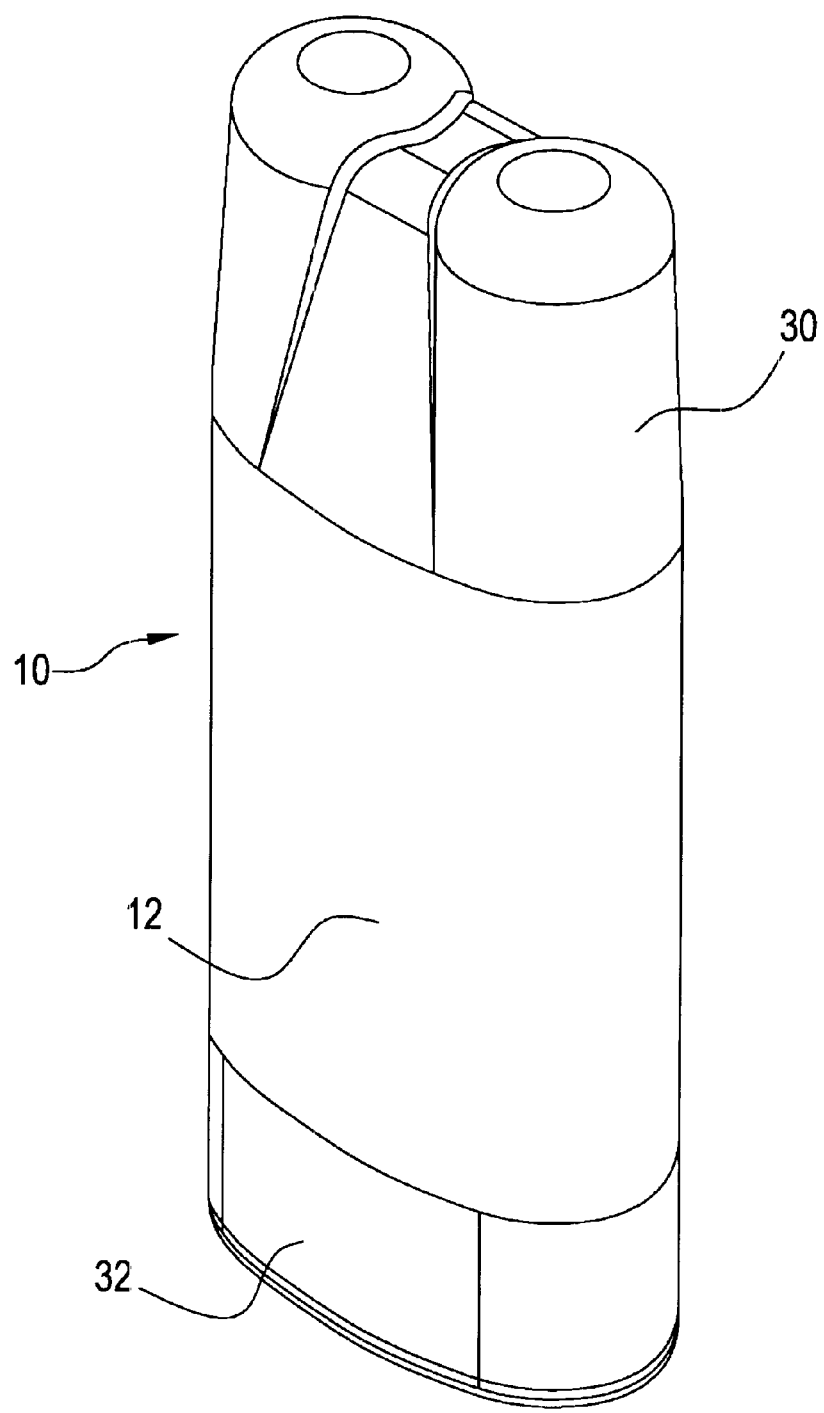
FIG. 1 is a plan view of a package according to the invention.
Figure 2:
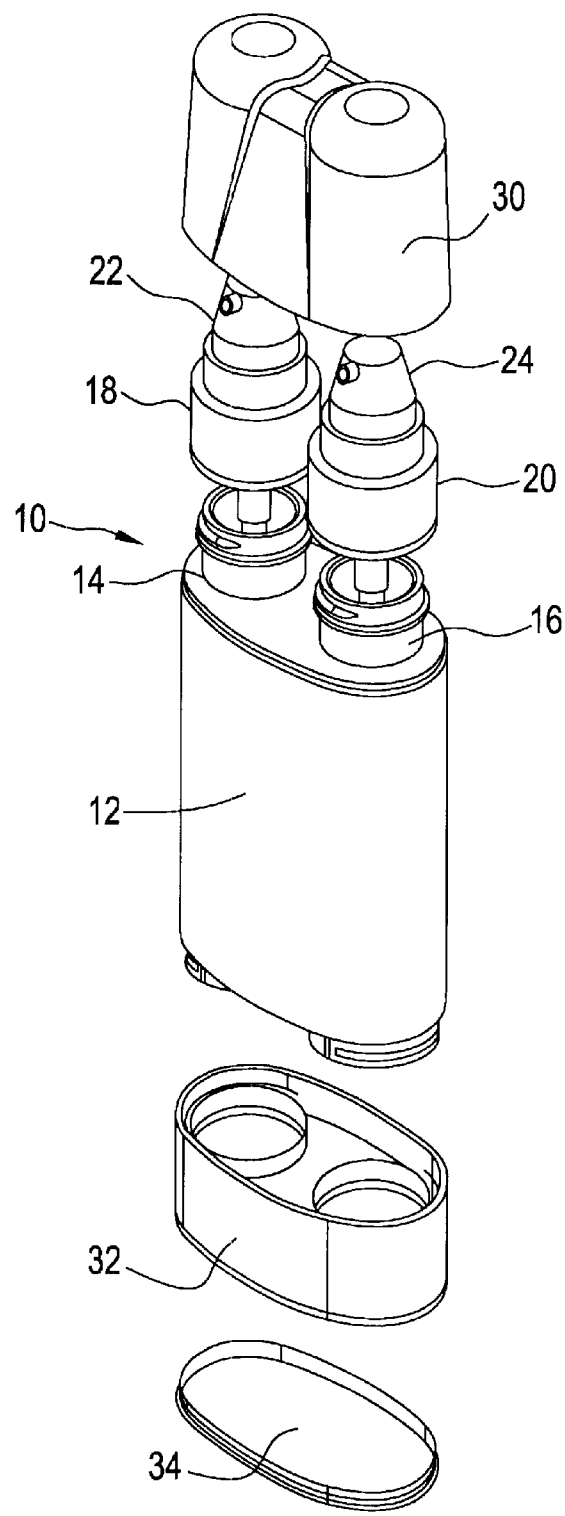
FIG. 2 is an exploded plan view of a package according to the invention.
Figure 3:
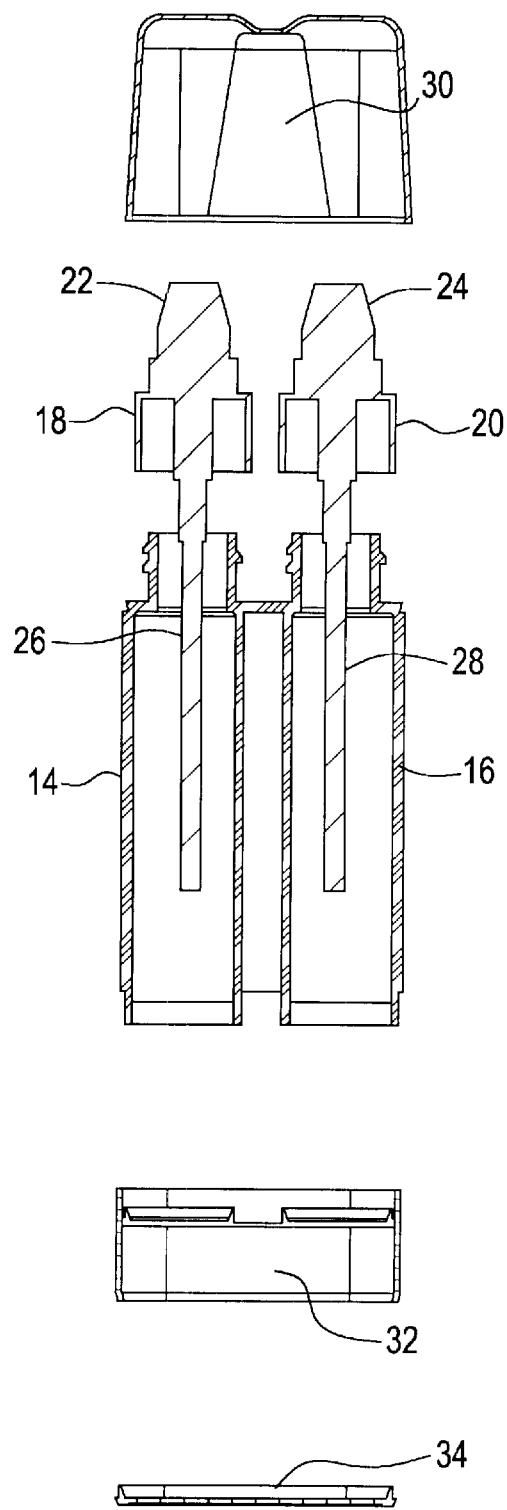
FIG. 3 is an exploded view in cross-section of a package according to the invention.

As shown in FIGS. 1, 2 and 3, package 10 includes an outer container 12 encasing two separate inner containers 14 and 16. Each of the inner containers includes a pump mechanism 18 and 20, respectively, of the type known in the art, including a spray head 22 and 24, and a tube 26 and 28. An upper cap 30 fits over the top of the package, protecting the spray heads 22 and 24, and a bottom closure 32 fits over the bottom of the inner containers 14 and 16. Bottom cap 34 serves a base for the package.

Container 14 contains an acne treatment composition comprising salicylic acid. A typical salicylic acid-containing composition is the following:

| ACNE GEL | |
|---|---|
| Component | % by weight |
| Salicylic Acid | 2.00 |
| Sodium Tetraborate | 1.50 |
| Natural Plant Extracts | 8.00 |
| Thickening Agent | 2.00 |
| Preservative & Fragrance | 0.30 |
| Neutralizing & Buffering Agent | 2.20 |
| Chelating Agent | 0.20 |
| S.D. Alcohol | 10.00 |
| Purified Water | Q.S. to 100 |

Because alcohol is an irritant, it may be desirable to formulate a composition with a minimum presence of alcohol, as is disclosed in copending application Ser. No. 09/888,766 filed on Jun. 25, 2001, using sodium tetraborate, sodium carbonate or sodium bicarbonate as a solubilizing agent. Such a composition is as follows:

| Component | % by weight |
|---|---|
| salicylic acid | 0.1–26 (0.5–2 preferred) |
| Sodium tetraborate and/or sodium carbonate and/or | 0.5–28 |

-continued

| Component | % by weight |
|---|---|
| sodium bicarbonate | |
| citric acid | 0.1–0.5 |
| tetrasodium EDTA | 0.1–0.5 |
| natural plant extracts | 8–24.5 |
| Preservative & fragrance | 0.5–1.0 |
| sodium or potassium hydroxide | 0.2–0.8 |
| thickening agent | 0.1–3.0 |
| Water | QS to 100% |

Container 16 contains an acne treatment composition comprising benzoyl peroxide. A typical composition is as follows:

ACNE LOTION

| Component | % by weight |
|---|---|
| Benzoyl Peroxide | 2.5–10.0 |
| Natural Plant Extracts | 8.0–24.0 |
| Thickening Agent | 0.3–3.0 |
| Preservative & Fragrance | 0.3–1.5 |
| Chelating Agent | 0.01–0.5 |
| Emollient/Esters/Humectant | 4.0–13.5 |
| pH Adjuster | 0.1–0.6 |
| Purified Water | Q.S. to 100 |

The emollient, esters, and humectant are included to prevent excessive dryness of the skin. The inclusion of PEG8/SMDI copolymer as emollient results in slow release of the active component over a long period of time.

The compositions in containers 14 and 16 may be in the form of a gel, lotion or cream. The pump is most suitable for use with higher viscosity products such as creams and gels.

The morning treatment is a clear solution of salicylic acid which does not leave a residue or film on the skin and keeps pores unclogged. The evening treatment is a benzoyl peroxide lotion which clear up breakouts of acne and helps prevent further breakouts. Since the benzoyl peroxide lotion is more visible when applied to the skin, and is photosensitive, it is better applied before bedtime.

The affected area should be thoroughly cleaned before applying any medication. The morning treatment may be applied to the skin once during the day, or as directed by a doctor. The evening treatment may be applied before bedtime, for the reasons noted above.

The combination of treatments according to the invention is preferable to a single treatment, as it lessens the damage done to the skin by the conditions treated, and covers a wider range of problems.

What is claimed is:

1. A dual regimen acne treatment package, comprising:
   an outer container;
   partially encased within the outer container, first and second inner containers which are separate from each other, each of said inner containers having a dispensing means for individually dispensing an acne treatment composition contained therein, and which extends outside of said outer container so that each dispensing means is exposed for use;
   the first said inner container containing a solubilized salicylic acid acne treatment composition; and
   the second said inner container containing a solubilized benzoyl peroxide acne treatment composition.

2. A package according to claim 1, additionally comprising at least one removable cap covering and protecting the dispensing means which are exposed for use.

3. A package according to claim 1, wherein the first and second inner containers are disposed parallel to each other within the package.

4. A package according to claim 1, wherein the dispensing means are pump dispensing means.

5. A package according to claim 1, wherein the first container contains a solubilized salicylic acid acne treatment composition comprising about 0.5–2% by weight salicylic acid, and the second container contains a solubilized benzoyl peroxide acne treatment composition comprising about 2.5–10% by weight benzoyl peroxide.

6. A package according to claim 1, wherein the first container contains, in % by weight:

| | |
|---|---|
| salicylic acid | 0.1–26 |
| Sodium tetraborate and/or sodium carbonate and/or sodium bicarbonate | 0.5–28 |
| citric acid | 0.1–0.5 |
| tetrasodium EDTA | 0.1–0.5 |
| natural plant extracts | 8–24.5 |
| Preservative & fragrance | 0.5–1.0 |
| sodium or potassium hydroxide | 0.2–0.8 |
| thickening agent | 0.1–3.0 |
| Water | QS to 100%. |

7. A package according to claim 6, wherein the salicylic acid is present in an amount of about 0.5–2% by weight.

8. A package according to claim 1, wherein the second container contains, in % by weight:

| | |
|---|---|
| Benzoyl Peroxide | 2.5–10.0 |
| Natural Plant Extracts | 8.0–24.0 |
| Thickening Agent | 0.3–3.0 |
| Preservative & Fragrance | 0.3–1.5 |
| Chelating Agent | 0.01–0.5 |
| Emollient/Esters/Humectant | 4.0–13.5 |
| pH Adjuster | 0.1–0.6 |
| Purified Water | QS to 100. |

* * * * *